(12) United States Patent
Wang et al.

(10) Patent No.: US 10,088,429 B2
(45) Date of Patent: Oct. 2, 2018

(54) MEASUREMENT APPARATUS AND OPERATING METHOD THEREOF

(71) Applicant: Crystalvue medical corporation, Taoyuan (TW)

(72) Inventors: William Wang, Taoyuan (TW); Meng-Shin Yen, Taipei (TW); Chung-Cheng Chou, Luzhu Township (TW); Chung-Ping Chuang, Taoyuan (TW)

(73) Assignee: Crystalvue Medical Corporation, Taoyuan (TW)

( * ) Notice: Subject to any disclaimer, the term of this patent is extended or adjusted under 35 U.S.C. 154(b) by 44 days.

(21) Appl. No.: 15/215,082

(22) Filed: Jul. 20, 2016

(65) Prior Publication Data

US 2017/0023486 A1    Jan. 26, 2017

Related U.S. Application Data

(60) Provisional application No. 62/194,886, filed on Jul. 21, 2015.

(51) Int. Cl.
*G01N 21/84* (2006.01)
*A61B 3/107* (2006.01)
*A61B 3/12* (2006.01)
*A61B 3/16* (2006.01)

(52) U.S. Cl.
CPC ............. *G01N 21/84* (2013.01); *A61B 3/107* (2013.01); *A61B 3/1208* (2013.01); *A61B 3/16* (2013.01)

(58) Field of Classification Search
CPC .. G01N 21/84; A61B 3/10; A61B 3/12; A61B 3/16; A61B 3/165; A61B 3/1208; A61B 3/107

See application file for complete search history.

(56) References Cited

U.S. PATENT DOCUMENTS

| | | | | |
|---|---|---|---|---|
| 5,187,506 A * | 2/1993 | Carter | ................... | A61B 3/112 351/205 |
| 5,946,075 A * | 8/1999 | Horn | ..................... | A61B 3/022 351/237 |
| 7,871,378 B1 * | 1/2011 | Chou | ..................... | A61B 3/165 600/398 |
| 8,824,779 B1 * | 9/2014 | Smyth | .................. | G06K 9/0061 382/100 |
| 2002/0135737 A1 * | 9/2002 | Petrali | ..................... | A61B 3/063 351/223 |

(Continued)

*Primary Examiner* — John Lee
(74) *Attorney, Agent, or Firm* — Patterson + Sheridan, LLP (57) ABSTRACT

A measurement apparatus used to measure an object is disclosed. The measurement apparatus includes at least one sensing unit, a first optical module, a second optical module, a data processing unit and at least one prompting unit. The at least one sensing unit is disposed near the object to perform a contact or proximity sensing on the object. The first optical module is disposed near the object and adjacent to the at least one sensing unit. The first optical module includes at least one lens unit. The second optical module and the object are disposed at opposite sides of the first optical module. The second optical module includes a light source and at least one optical component. The data processing unit is coupled to at least one sensing unit. The at least one prompting unit is coupled to the data processing unit.

11 Claims, 8 Drawing Sheets

(56) References Cited

U.S. PATENT DOCUMENTS

| | | | |
|---|---|---|---|
| 2004/0087849 A1* | 5/2004 | Masaki | A61B 3/165 600/401 |
| 2005/0030473 A1* | 2/2005 | Fahrenkrug | A61B 3/1005 351/200 |
| 2007/0055121 A1* | 3/2007 | Luce | A61B 3/16 600/405 |
| 2008/0259276 A1* | 10/2008 | Roberts | A61B 3/165 351/212 |
| 2011/0007144 A1* | 1/2011 | De Paz Sicam | A61B 3/107 348/78 |
| 2011/0118585 A1* | 5/2011 | Ishii | A61B 3/16 600/401 |
| 2011/0313273 A1* | 12/2011 | Koest | A61B 3/165 600/401 |
| 2011/0319791 A1* | 12/2011 | Harry | A61B 5/0053 600/587 |
| 2012/0136285 A1* | 5/2012 | Korb | A61F 7/12 601/15 |
| 2012/0253165 A1* | 10/2012 | Yen | A61B 3/16 600/398 |
| 2012/0265047 A1* | 10/2012 | Yen | A61B 3/165 600/405 |
| 2012/0287255 A1* | 11/2012 | Ignatovich | A61B 3/1208 348/78 |
| 2013/0165762 A1* | 6/2013 | Choo | A61B 3/16 600/398 |
| 2014/0078467 A1* | 3/2014 | Su | A61B 3/1208 351/207 |
| 2014/0092361 A1* | 4/2014 | Takii | A61B 3/165 351/211 |
| 2014/0267668 A1* | 9/2014 | Ignatovich | A61B 3/14 348/78 |
| 2014/0275936 A1* | 9/2014 | Huang | A61B 3/16 600/398 |
| 2014/0307227 A1* | 10/2014 | Shibahara | A61B 3/107 351/206 |
| 2014/0320815 A1* | 10/2014 | Steinmueller | A61B 3/102 351/206 |
| 2015/0009473 A1* | 1/2015 | Su | A61B 3/125 351/206 |
| 2015/0021228 A1* | 1/2015 | Su | A61B 3/14 206/570 |
| 2015/0245767 A1* | 9/2015 | Northcott | A61B 3/102 351/206 |
| 2015/0338914 A1* | 11/2015 | Andrysco | G06F 3/041 345/173 |
| 2016/0066786 A1* | 3/2016 | Kontiola | A61B 3/165 351/221 |
| 2017/0001032 A1* | 1/2017 | Samec | A61B 3/085 |
| 2017/0027444 A1* | 2/2017 | Rege | A61B 3/0008 |
| 2017/0071790 A1* | 3/2017 | Grenon | A61F 7/007 |
| 2017/0181626 A1* | 6/2017 | Shau | A61B 3/0025 |

* cited by examiner

MEASUREMENT APPARATUS AND OPERATING METHOD THEREOF

CROSS-REFERENCE TO RELATED APPLICATIONS

This application claims the benefit of U.S. provisional Patent Application Ser. No. 62/194,886 filed on Jul. 21, 2015 which is incorporated by reference in its entirety.

BACKGROUND OF THE INVENTION

Field of the Invention

This invention relates to a measurement apparatus, especially to a measurement apparatus and a measurement apparatus operating method applied to eyes.

Description of the Prior Art

With the progress of technology, various kinds of measurement apparatus applied to eyes, such as tonometer, biometer, fundus camera, corneal curvature detector and refractor, have been developed and widely used.

However, for the one to be tested, if he/she wants to do some measurements on his/her eyes currently, different kinds of measurement apparatuses should be used to do different kinds of measurements on his/her eyes; it is not only very time-consuming, but also the one to be tested cannot easily do self-measurement at any time. Obviously, although the above-mentioned eye measurement apparatuses have been developed, it is still very incontinent for the user to do measurement in practical applications and needed to be improved.

Therefore, the invention provides a multi-functional measurement apparatus capable of easily performing self-measurements for the one to be tested and an operating method thereof to overcome the problems occurred in the above-mentioned prior arts.

SUMMARY OF THE INVENTION

An embodiment of the invention is a measurement apparatus. In this embodiment, the measurement apparatus is used to measure an object. The measurement apparatus includes at least one sensing unit, a first optical module, a second optical module, a data processing unit and at least one prompting unit. The at least one sensing unit is disposed near the object to perform a contact or proximity sensing on the object. The first optical module is disposed near the object and adjacent to the at least one sensing unit. The first optical module includes at least one lens unit. The second optical module and the object are disposed at opposite sides of the first optical module. The second optical module includes a light source and at least one optical component. The data processing unit is coupled to at least one sensing unit. The at least one prompting unit is coupled to the data processing unit.

In an embodiment, the object is a living body or a non-living body.

In an embodiment, the at least one prompting unit includes a visual prompting unit configured to use changes of light or color to achieve a prompting function.

In an embodiment, the at least one prompting unit includes an audio prompting unit configured to use changes of audio frequency or volume to achieve a prompting function.

In an embodiment, the measurement apparatus further includes a display unit coupled to the data processing unit and configured to display a measurement result or a prompting message.

In an embodiment, the measurement apparatus further includes a handheld unit disposed out of the measurement apparatus and configured to be held by a user to perform measurement.

In an embodiment, the measurement apparatus further includes a manipulating unit disposed out of the measurement apparatus and configured to be manipulated by a user to switch or adjust functions of the measurement apparatus.

In an embodiment, the display unit has a touch function.

In an embodiment, the measurement apparatus further includes a replaceable unit replaceably disposed out of the at least one sensing unit and the first optical module to be contacted or adjacent to the object.

In an embodiment, the at least one sensing unit performs the contact or proximity sensing on the object through a sensing theorem of optics, electronics, mechanics or magnetism.

Another embodiment of the invention is a measurement apparatus operating method for operating a measurement apparatus to measure an object. In this embodiment, the measurement apparatus operating method includes steps of: confirming that the measurement apparatus aligns a center of the object and then the measurement apparatus starting to provide a force on the object; when the object is pressed by the force and changed from an original state to a pressed state, defining the force at this time as a reference force; reducing the force that the measurement apparatus provides on the object to be smaller than the reference force to obtain a first time needed for the object to be recovered from the pressed state to the original state and then calculate a first curvature of the object accordingly; increasing the force that the measurement apparatus provides on the object to be equal to the reference force to obtain a second time needed for the object to be changed from the original state to the pressed state and then calculate a second curvature of the object accordingly; and calculating a curvature and a physical characteristic of the object according to the first curvature and the second curvature of the object.

Compared to the prior art, the measurement apparatus and operating method thereof have the following advantages of:

(1) providing multiple kinds of eye measurement functions at the same time to save the time of the one to be tested;

(2) the one to be tested can easily hold the measurement apparatus by hand to do self-measurements on his/her eyes at any time;

(3) increasing the number of the sensors in the measurement apparatus to effectively improve the measurement data of the cornea curvature and characteristics;

(4) using the parameters of the one to be tested such as age, gender, area or race to effectively enhance the eye measurement efficiency and accuracy of the measurement apparatus.

The advantage and spirit of the invention may be understood by the following detailed descriptions together with the appended drawings.

DETAILED DESCRIPTION OF THE INVENTION

A preferred embodiment of the invention is a measurement apparatus. In this embodiment, the measurement apparatus is a hand-held multi-functional measurement apparatus capable of performing different kinds of measurements on an object (e.g., a living body or a non-living body), but not limited to this.

It should be noticed that, because the hand-held multi-functional measurement apparatus is easy to be held and operate, it can be not only operated by the operator to perform measurements on the position (e.g., eyes) to be tested of the one to be tested, but also operated by the one to be tested to perform self-measurements on his/her own eyes. It is very convenient.

Figure 1:
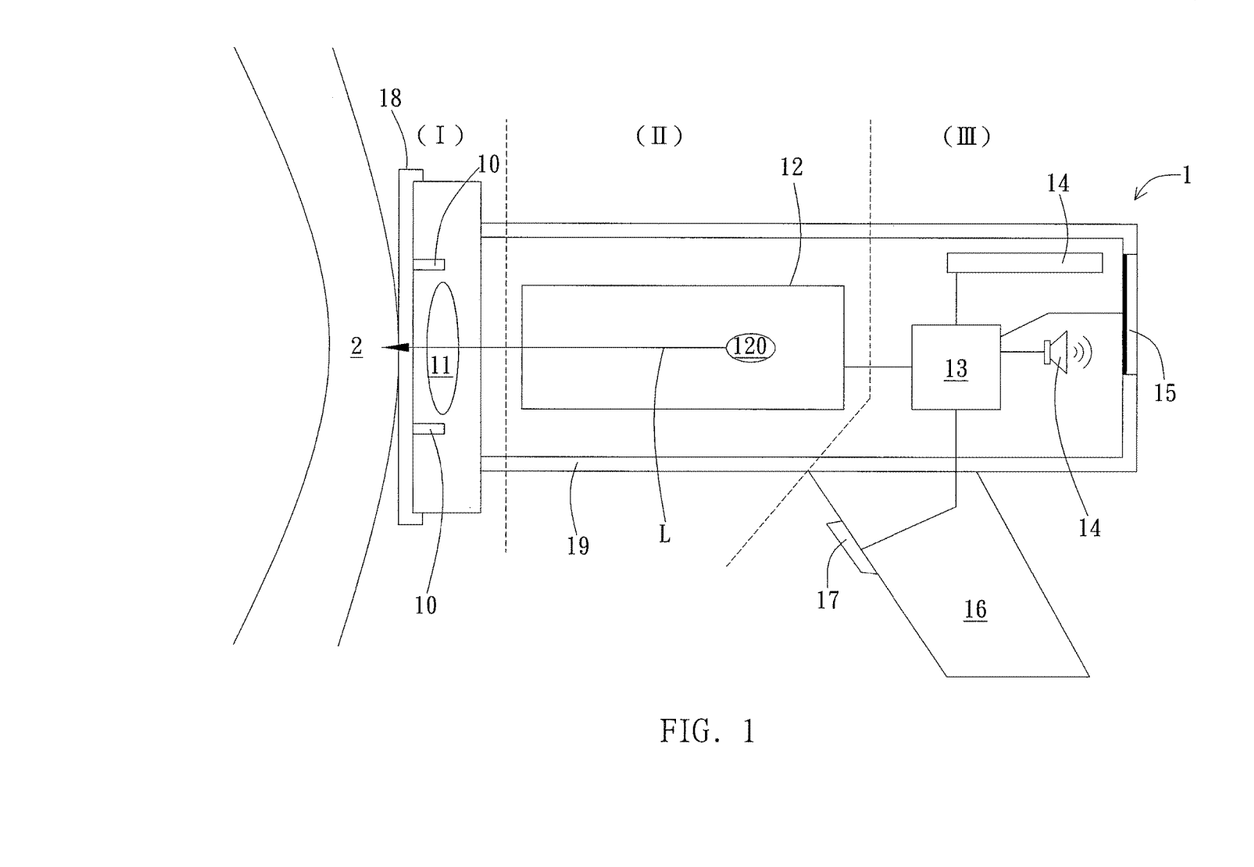
FIG. 1 illustrates a schematic diagram of the measurement apparatus in a preferred embodiment of the invention.

At first, please refer to FIG. 1. FIG. 1 illustrates a schematic diagram of the measurement apparatus in a preferred embodiment of the invention.

As shown in FIG. 1, the hand-held multi-functional measurement apparatus 1 used to perform measurements on the object (e.g., the eyes of the one to be tested) 2 can include at least one sensing unit 10, a first optical module 11, a second optical module 12, a data processing unit 13, at least one prompting unit 14, a display unit 15, a hand-held unit 16, a manipulating unit 17, a replaceable unit 18 and a housing 19. Wherein, the second optical module 12 includes a light source 120 used to emit an incident light L; the at least one sensing unit 10 includes two sensing units 10, but not limited to this.

In this embodiment, the two sensing units 10 are disposed near the object 2, so that the two sensing units 10 can perform a contact or proximity sensing on the object 2. That is to say, the hand-held multi-functional measurement apparatus 1 of the invention can use the two sensing units 10 to sense whether the hand-held multi-functional measurement apparatus 1 itself is already near the object 2 or contacted with the surface of the object 2. Therefore, it can provide the functions of contact determination, alignment determination and cornea curvature determination.

In detail, the sensing unit 10 can include transparent conductor or oblique conductor and its shape can be a sheet shape or a ring shape and the sensing is performed according to its resistance change or capacitance change, but not limited to this.

In practical applications, the sensing units 10 can perform the contact or proximity sensing on the object 2 through a sensing theorem of optics, electronics, mechanics or magnetism. That is to say, the sensing units 10 of the invention can be proximity sensors, but not limited to this.

The first optical module 11 includes at least one lens unit and the first optical module 11 is disposed near the object 2 and adjacent to the at least one sensing unit 10. For example, as shown in FIG. 1, the two sensing units 10 and the first optical module 11 are both disposed near the object 2 and the two sensing units 10 are disposed at two sides of the first optical module 11 respectively, but not limited to this.

The second optical module 12 and the object 2 are disposed at opposite sides of the first optical module 11. That is to say, the first optical module 11 is correspondingly disposed between the object 2 and the second optical module 12, so that the incident light L emitted from the light source of the second optical module 12 can pass through the lens unit in the first optical module 11 and then emitted toward the object 2.

In fact, the light source 120 can be any light sources suitable for practical needs based on the wavelength, frequency or energy of the incident light emitted by the light source 120. In addition, the second optical module 12 can not only include the light source 120, but also further include at least one optical component (e.g., lens), but not limited to this.

The data processing unit 13 is coupled to the second optical module 12, the sensing units 10, the at least one prompting unit 14, the display unit 15 and the manipulating unit 17 respectively. The data processing unit 13 is used to operate and calculate the sensed data and then output a prompting signal to the prompting unit 14 and output a display signal to the display unit 15 respectively according to the sensing result. In fact, the data processing unit 13 can be a central processing unit (CPU) or a microprocessor, but not limited to this.

The at least one prompting unit 14 is coupled to the data processing unit 13 and used to provide a prompting message to the one to be test or the operator. In practical applications, the at least one prompting unit 14 can include a visual prompting unit (e.g., a LED) which can use changes of light or color to achieve a prompting function; the at least one prompting unit 14 can include an audio prompting unit (e.g., a loudspeaker) which can use changes of audio frequency or volume to achieve a prompting function, but not limited to these cases.

The display unit 15 is coupled to the data processing unit 13 and used to display an image of the object, a measurement result or a prompting message to inform the user (e.g., the one to be tested or the operator). In practical applications, the display unit 15 can have a touch function, for example, a touch panel for the user (e.g., the one to be tested or the operator) to perform the touch operation.

In addition, the handheld unit 16 is disposed out of the measurement apparatus 1 and it is held by the user (e.g., the one to be tested or the operator) to perform measurement. In fact, the handheld unit 16 can be designed as a grip for the user (e.g., the one to be tested or the operator) to hold.

The manipulating unit 17 is disposed out of the measurement apparatus 1 and used to be manipulated by the user (e.g., the one to be tested or the operator) to switch or adjust the functions of the measurement apparatus 1. In fact, the manipulating unit 17 can be designed as a button for the user (e.g., the one to be tested or the operator) to press. It should be noticed that, if the display unit 15 has the touch function, then the user (e.g., the one to be tested or the operator) can switch or adjust different functions of the measurement apparatus 1 through touching the display unit 15 directly, but not limited to this.

The replaceable unit 18 is replaceably disposed at the forefront of the measurement apparatus 1 (namely disposed out of the at least one sensing unit 10 and the first optical module 11) to be contacted or adjacent to the object 2. In practical applications, the replaceable unit 18 can be designed as a disposable component or can be removed to be disinfected and then reused. In addition, the replaceable unit 18 can be deformed or added anesthetic agents based on practical needs, but not limited to this.

In this embodiment, the at least one sensing unit 10, the first optical module 11, the second optical module 12, the data processing unit 13 and the at least one prompting unit 14 are all disposed in the housing 19, but not limited to this.

In fact, the entire structure of the measurement apparatus 1 can be divided into three main parts, wherein the first part (I) includes the sensing unit 10, the first optical module 11 and the replaceable unit 18 which are disposed at the forefront of the measurement apparatus 1; the second part (II) includes the second optical module 12 which is disposed at the middle of the measurement apparatus 1; the third part (III) includes the data processing unit 13, the at least one prompting unit 14, the display unit 15, the hand-held unit 16 and the manipulating unit 17 which is disposed at the rearmost of the measurement apparatus 1.

Figure 2:
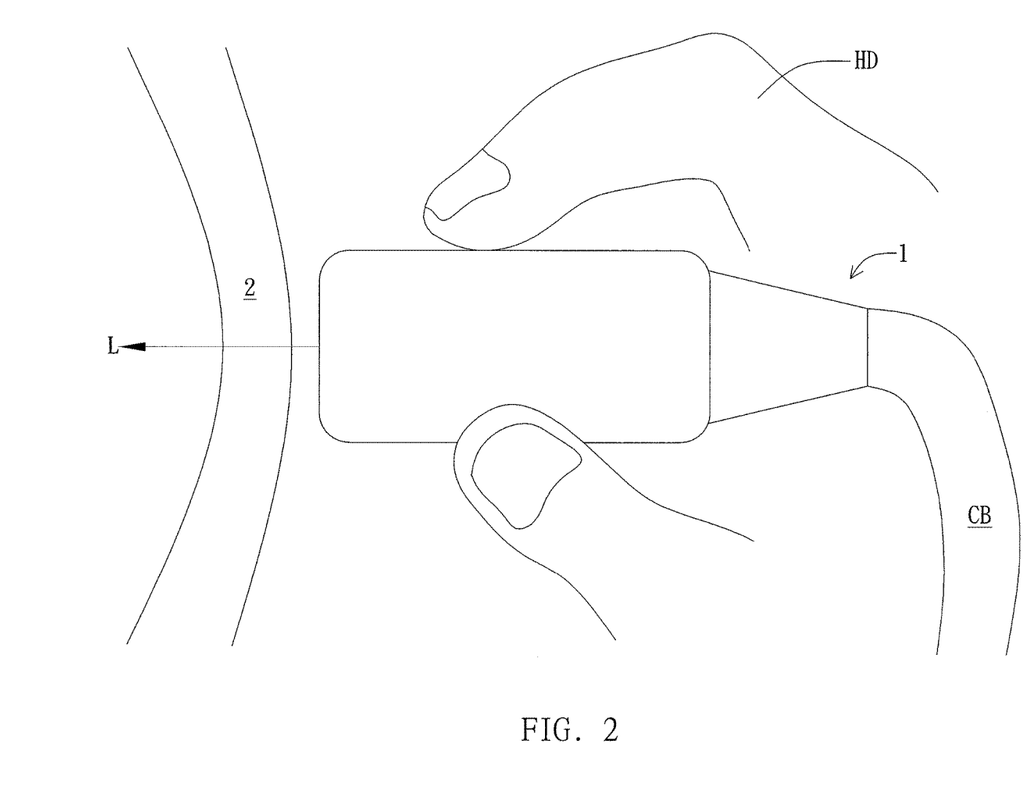
FIG. 2 illustrates a schematic diagram of the measurement apparatus having small volume and convenient to be held to do different measurements.

In order to reduce the volume of the measurement apparatus 1, the second part (II) and the third part (III) of the measurement apparatus 1 can be elastically designed. For example, as shown in FIG. 2, only the at least one sensing unit 10, the first optical module 11 and the second optical module 12 disposed in the housing 19 of the measurement apparatus 1 and they can connected to a host (not shown in FIG. 2) through a transmission line CB, and the data processing unit 13, the at least one prompting unit 14 and the display unit 15 can be disposed in the host, so that the volume of the measurement apparatus 1 can be reduced and the one to be tested can easily use his/her hand to hold the measurement apparatus 1 to do the self-measurement anytime and adjust the measuring angle of the measurement apparatus 1, but not limited to this.

Figure 3A:
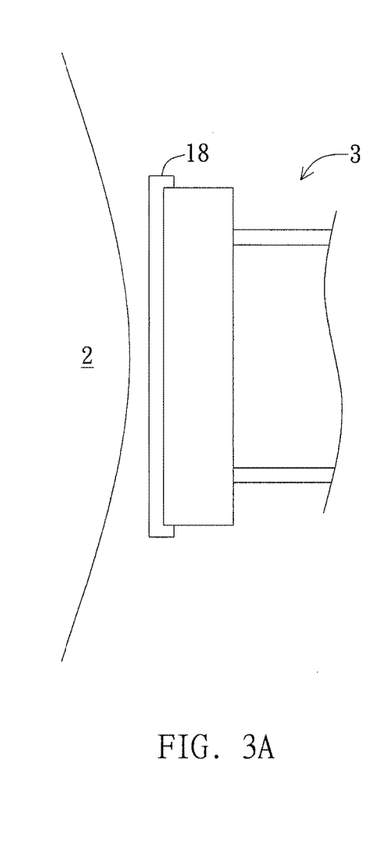
FIG. 3A~FIG. 3C illustrate schematic diagrams of the measurement apparatus performing different measurements respectively.
Figure 3B:
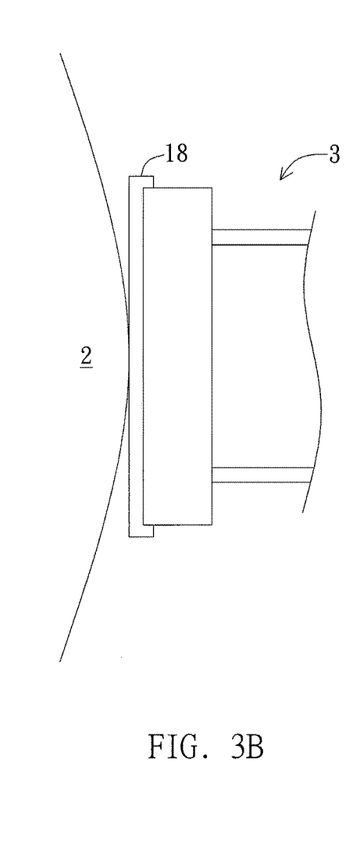
Figure 3C:
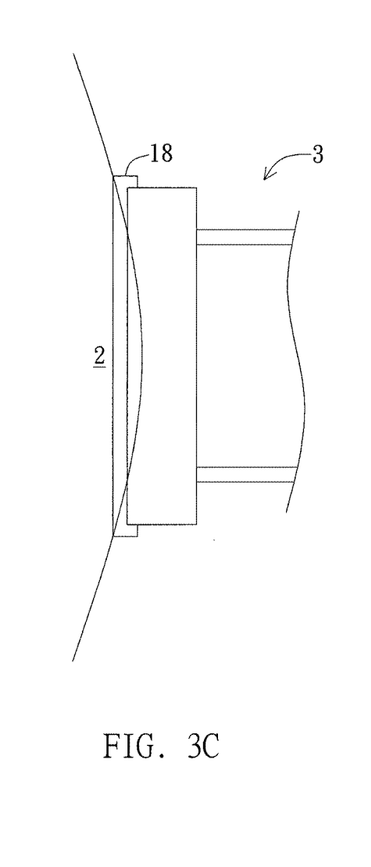

Please refer to FIG. 3A~FIG. 3C. FIG. 3A~FIG. 3C illustrate schematic diagrams of the measurement apparatus performing different measurements respectively. As shown in FIG. 3A~FIG. 3C, the measurement apparatus 3 can finish different kinds measurements such as eye axis measurement, fundus measurement, intraocular pressure measurement and corneal curvature measurement by using different ways such as the forefront replaceable unit 18 to approach the object 2, contact with the surface of the object 2 or provide force on the surface of the object 2 to deform it.

Figure 4A:
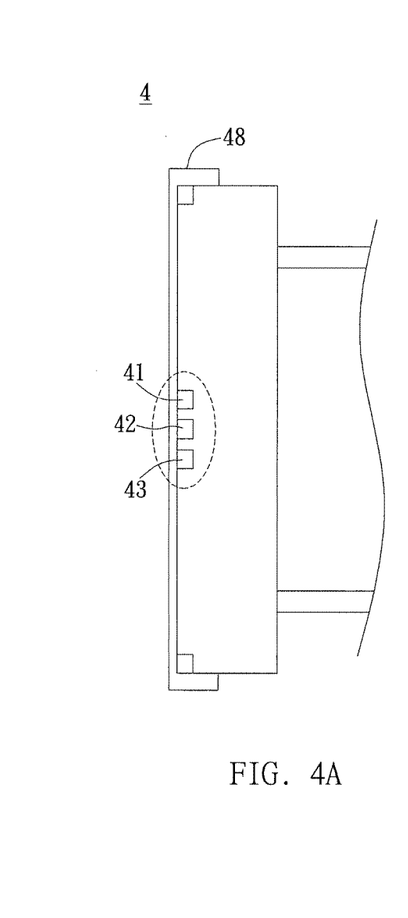
FIG. 4A~FIG. 4C illustrate schematic diagrams of the measurement apparatus using its sensing unit to align the eye axis.
Figure 4B:
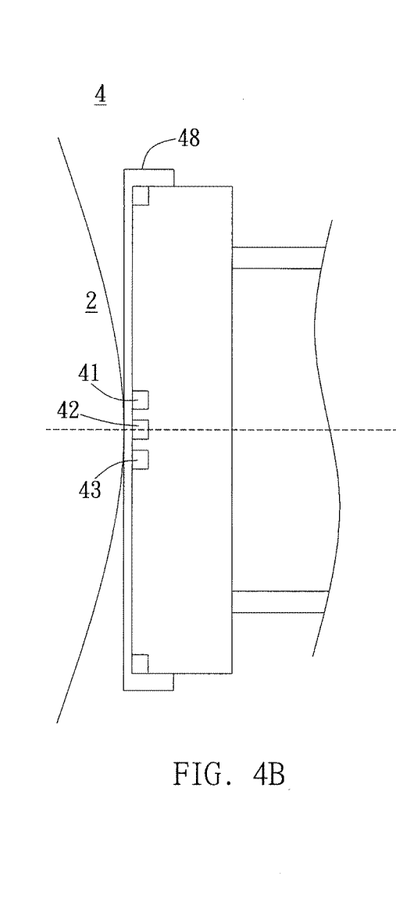
Figure 4C:
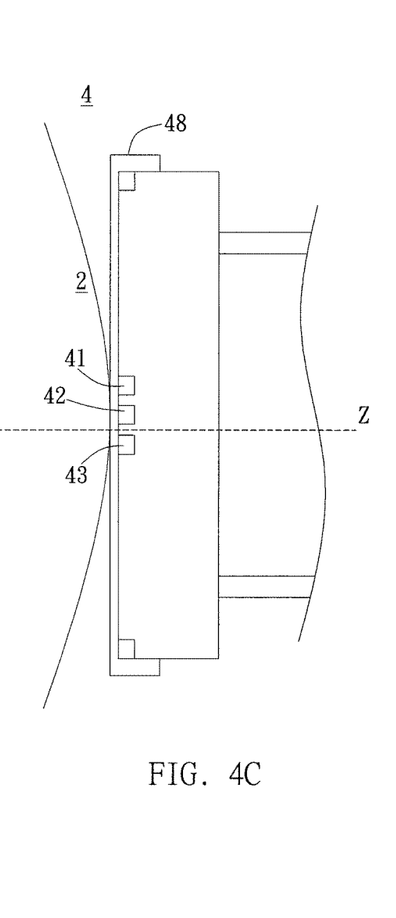

Please refer to FIG. 4A~FIG. 4C. FIG. 4A~FIG. 4C illustrate schematic diagrams of the measurement apparatus using its sensing unit to align the eye axis. As shown in FIG. 4A, three sensing units 41~43 are disposed at the center part of the measurement apparatus 4. When the measurement apparatus 4 performs eye axis alignment, for example, the measurement apparatus 4 can use one of the sensing units 41~43 (e.g., the sensing unit 42) to align the eye axis Z (as shown in FIG. 4B) or use the gap between two of the sensing units 41~43 (e.g., the gap between the sensing units 42 and 43) to be corresponding to the eye axis Z (as shown in FIG. 4C), but not limited to this.

Figure 5A:
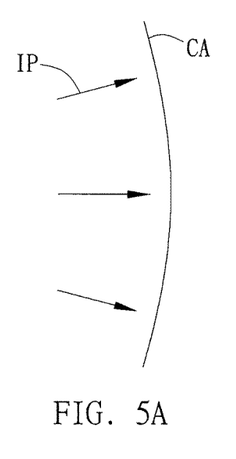
FIG. 5A~FIG. 5D illustrate schematic diagrams of different combinations of corneal curvature and intraocular pressure respectively.
Figure 5B:
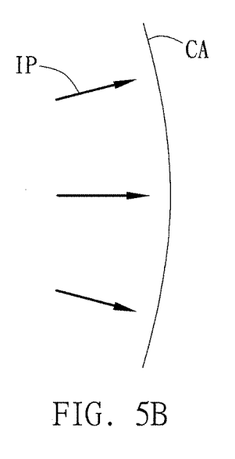
Figure 5C:
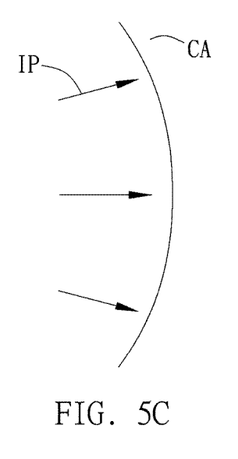
Figure 5D:
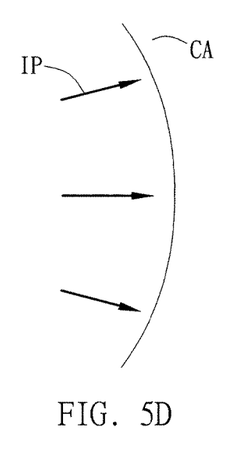

Please refer to FIG. 5A~FIG. 5D. FIG. 5A~FIG. 5D illustrate schematic diagrams of different combinations of corneal curvature and intraocular pressure respectively. As shown in FIG. 5A~FIG. 5D, FIG. 5A illustrates the combination of relatively small curvature of corneal CA and relatively small intraocular pressure IP; FIG. 5B illustrates the combination of relatively small curvature of corneal CA and relatively large intraocular pressure IP; FIG. 5C illustrates the combination of relatively large curvature of corneal CA and relatively small intraocular pressure IP; FIG. 5D illustrates the combination of relatively large curvature of corneal CA and relatively large intraocular pressure IP.

Figure 6A:
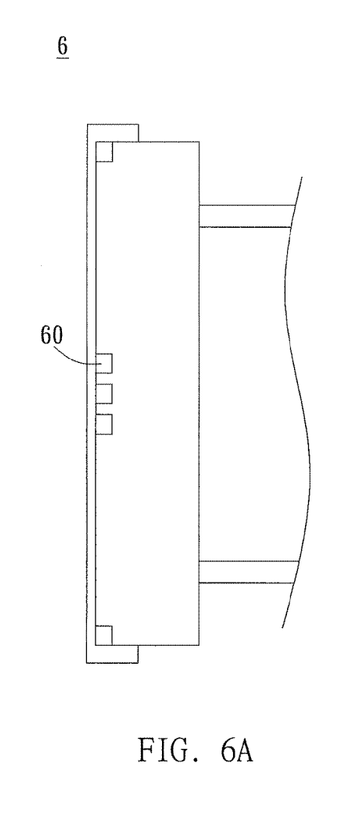
FIG. 6A~FIG. 6B illustrate schematic diagrams of effectively improving the measurement data of the cornea curvature and characteristics by increasing the number of the sensors in the measurement apparatus.
Figure 6B:
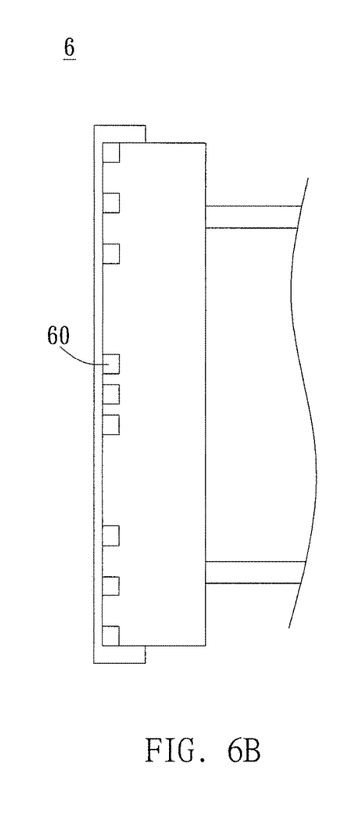

Please refer to FIG. 6A~FIG. 6B. FIG. 6A~FIG. 6B illustrate schematic diagrams of effectively improving the measurement data of the cornea curvature and characteristics by increasing the number of the sensors in the measurement apparatus. As shown in FIG. 6A~FIG. 6B, when the number of the sensing units 60 of the measurement apparatus 6 is increased from 5 in FIG. 6A to 9 in FIG. 6B, the measurement apparatus 6 can provide more accurate measurement results to further effectively improve the sensing data of the corneal curvature and characteristics, even the asymmetric differences can be determined. In addition, the measurement apparatus of the invention can effectively enhance the eye measurement efficiency and accuracy of the measurement apparatus by using the parameters of the one to be tested such as age, gender, area or race.

Figure 7A:
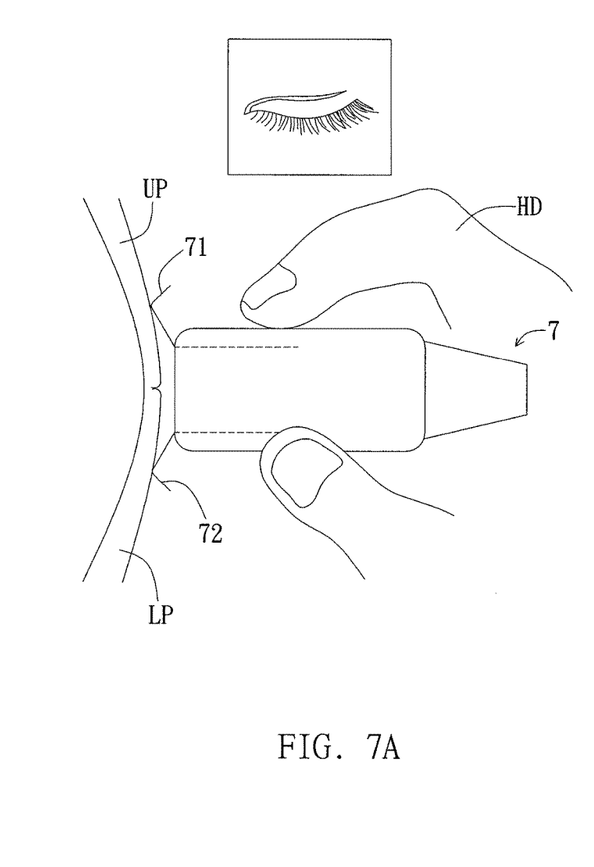
FIG. 7A~FIG. 7B illustrate schematic diagrams of the measurement apparatus further including an auxiliary unit to open the eyelids.
Figure 7B:
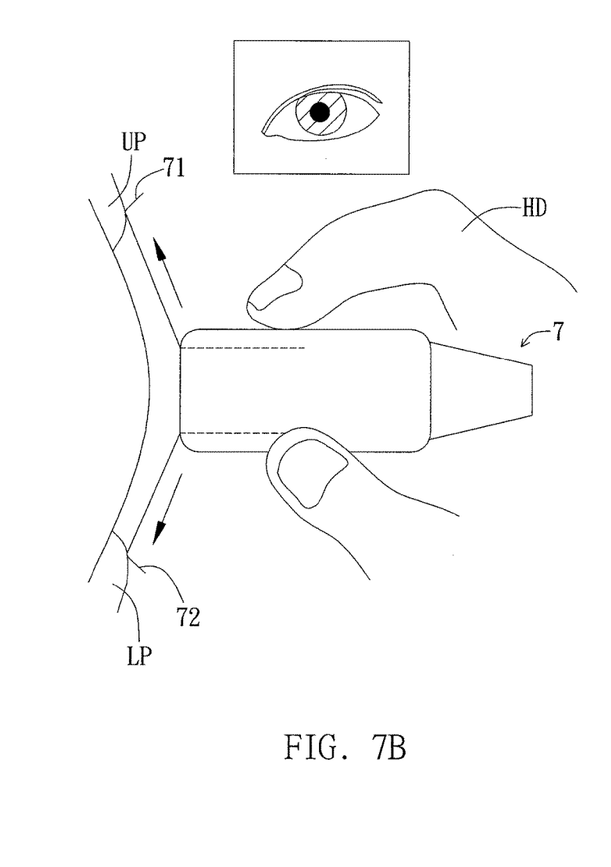

Then, please refer to FIG. 7A~FIG. 7B. FIG. 7A~FIG. 7B illustrate schematic diagrams of the measurement apparatus further including an auxiliary unit to separate the eyelids (the upper eyelid and the lower eyelid) of an eye. As shown in FIG. 7A, when the upper eyelid UP and the lower eyelid LP of the eye to be tested close up, the user can use his/her hand HD to hold the measurement apparatus 7 to withstand the upper eyelid UP and the lower eyelid LP of the eye to be tested through the upper auxiliary unit 71 and the lower auxiliary unit 72 respectively. As shown in FIG. 7B, when the upper auxiliary unit 71 and the lower auxiliary unit 72 of the measurement apparatus 7 withstand the upper eyelid UP and the lower eyelid LP of the eye to be tested respectively, the measurement apparatus 7 can control the upper auxiliary unit 71 to move the upper eyelid UP upward and control the lower auxiliary unit 72 to move the lower eyelid LP downward to separate the upper eyelid UP and the lower eyelid LP of the eye to be tested.

Figure 8:
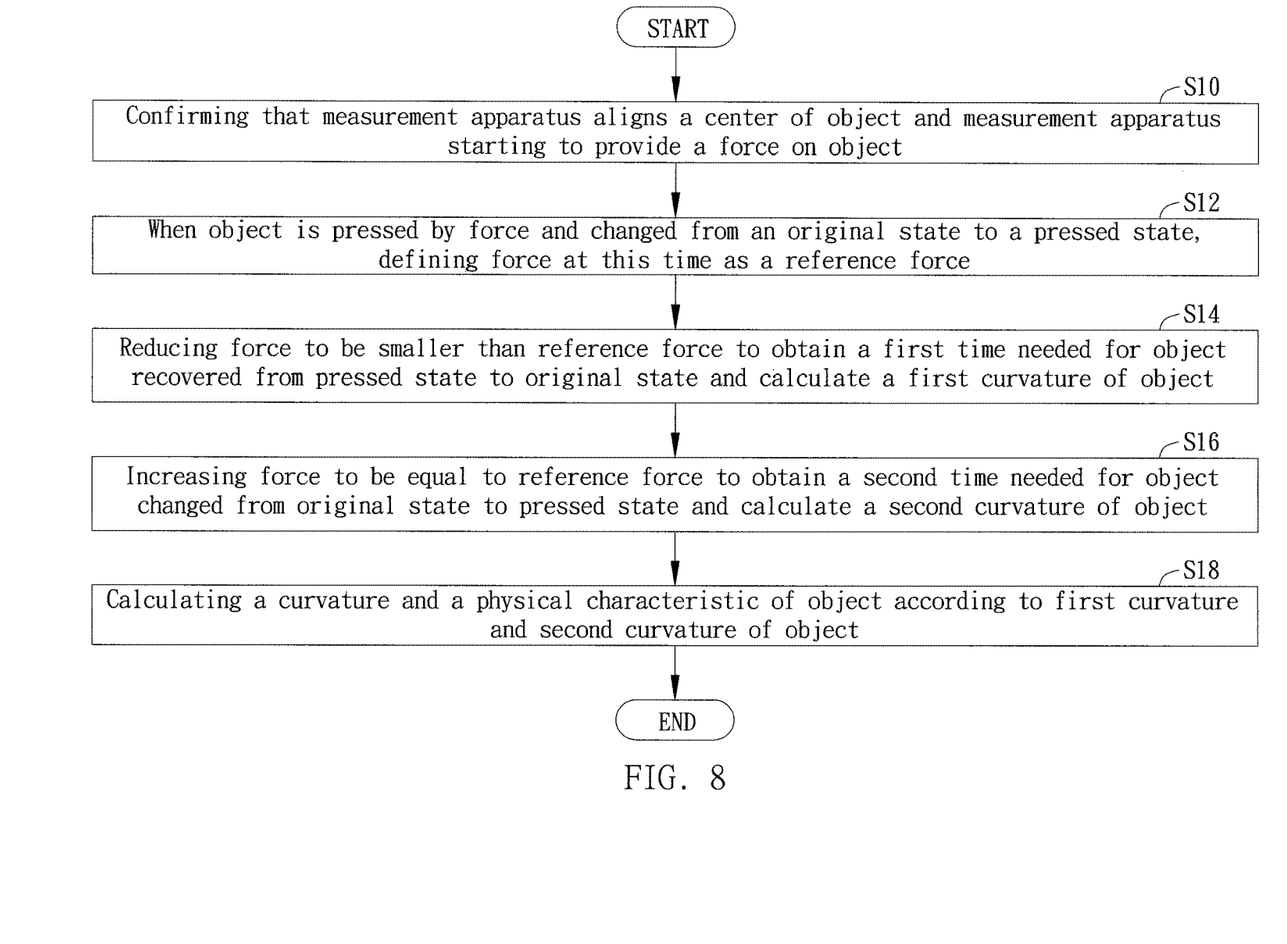
FIG. 8 illustrates a flowchart of the measurement apparatus operating method in another embodiment of the invention.

Another embodiment of the invention is a measurement apparatus operating method. In this embodiment, the measurement apparatus operating method is used for operating a measurement apparatus to measure an object. Please refer to FIG. 8. FIG. 8 illustrates a flowchart of the measurement apparatus operating method in another embodiment of the invention.

As shown in FIG. 8, the measurement apparatus operating method includes steps of:

Step S10: confirming that the measurement apparatus aligns a center of the object and then the measurement apparatus starting to provide a force on the object;

Step S12: when the object is pressed by the force and changed from an original state to a pressed state, defining the force at this time as a reference force;

Step S14: reducing the force that the measurement apparatus provides on the object to be smaller than the reference force to obtain a first time needed for the object to be recovered from the pressed state to the original state and then calculate a first curvature of the object accordingly;

Step S16: increasing the force that the measurement apparatus provides on the object to be equal to the reference force to obtain a second time needed for the object to be changed from the original state to the pressed state and then calculate a second curvature of the object accordingly; and Step S18: calculating a curvature and a physical characteristic of the object according to the first curvature and the second curvature of the object.

In practical applications, the invention can obtain the cornea curvature and the cornea characteristics such as viscosity and elasticity of the eyes of the one to be tested through the above-mentioned measurement apparatus operating method, but not limited to this.

Compared to the prior art, the measurement apparatus and operating method thereof have the following advantages of:

(1) providing multiple kinds of eye measurement functions at the same time to save the time of the one to be tested;

(2) the one to be tested can easily hold the measurement apparatus by hand to do self-measurements on his/her eyes at any time;

(3) increasing the number of the sensors in the measurement apparatus to effectively improve the measurement data of the cornea curvature and characteristics;

(4) using the parameters of the one to be tested such as age, gender, area or race to effectively enhance the eye measurement efficiency and accuracy of the measurement apparatus.

With the example and explanations above, the features and spirits of the invention will be hopefully well described. Those skilled in the art will readily observe that numerous modifications and alterations of the device may be made while retaining the teaching of the invention. Accordingly, the above disclosure should be construed as limited only by the metes and bounds of the appended claims.

What is claimed is:

1. A measurement apparatus used to measure an object, the measurement apparatus comprising:
    a plurality of sensing units disposed near the object and configured to perform a contact or proximity sensing on the object;
    a first optical module disposed near the object and adjacent to the plurality of sensing units, wherein the first optical module comprises at least one lens unit;
    a second optical module, wherein the second optical module and the object are disposed at opposite sides of the first optical module, and the second optical module comprises a light source and at least one optical component;
    an upper auxiliary unit and a lower auxiliary unit;
    a data processing unit coupled to the plurality of sensing units; and
    at least one prompting unit coupled to the data processing unit;
    wherein the object is an eye having an upper eyelid and a lower eyelid, when the upper auxiliary unit and the lower auxiliary unit withstand the upper eyelid and the lower eyelid of the eye respectively, the measurement apparatus controls the upper auxiliary unit to move the upper eyelid upward and controls the lower auxiliary unit to move the lower eyelid downward to separate the upper eyelid and the lower eyelid, and a gap between two sensing units of the plurality of sensing units is corresponding to an eye axis of the eye.

2. The measurement apparatus of claim 1, wherein the at least one prompting unit comprises a visual prompting unit configured to use changes of light or color to achieve a prompting function.

3. The measurement apparatus of claim 1, wherein the at least one prompting unit comprises an audio prompting unit configured to use changes of audio frequency or volume to achieve a prompting function.

4. The measurement apparatus of claim 1, further comprising:
    a display unit coupled to the data processing unit and configured to display a measurement result or a prompting message.

5. The measurement apparatus of claim 1, further comprising:
    a handheld unit disposed out of the measurement apparatus and configured to be held by a user to perform measurement.

6. The measurement apparatus of claim 1, further comprising:
    a manipulating unit disposed out of the measurement apparatus and configured to be manipulated by a user to switch or adjust functions of the measurement apparatus.

7. The measurement apparatus of claim 4, wherein the display unit has a touch function.

8. The measurement apparatus of claim 1, further comprising:
    a replaceable unit replaceably disposed out of the plurality of sensing units and the first optical module to be contacted or adjacent to the object.

9. The measurement apparatus of claim 1, wherein the plurality of sensing units performs the contact or proximity sensing on the object through a sensing theorem of optics, electronics, mechanics or magnetism.

10. The measurement apparatus of claim 1, wherein the plurality of sensing units comprises a transparent conductor or an opaque conductor and configured to sense changes of resistance or capacitance.

11. A measurement apparatus operating method for operating a measurement apparatus to measure an object, the measurement apparatus operating method comprising steps of:
    confirming that the measurement apparatus aligns a center of the object and then the measurement apparatus starting to provide a force on the object;
    when the object is pressed by the force and changed from an original state to a pressed state, defining the force at this time as a reference force; reducing the force that the measurement apparatus provides on the object to be smaller than the reference force to obtain a first time needed for the object to be recovered from the pressed state to the original state and then calculate a first curvature of the object accordingly;
    increasing the force that the measurement apparatus provides on the object to be equal to the reference force to obtain a second time needed for the object to be changed from the original state to the pressed state and then calculate a second curvature of the object accordingly; and
    calculating a curvature and a physical characteristic of the object according to the first curvature and the second curvature of the object;
    wherein the object is an eye having an upper eyelid and a lower eyelid, the measurement apparatus comprises a plurality of sensing units, an upper auxiliary unit and a lower auxiliary unit, when the upper auxiliary unit and the lower auxiliary unit withstand the upper eyelid and the lower eyelid of the eye respectively, the measurement apparatus controls the upper auxiliary unit to move the upper eyelid upward and controls the lower auxiliary unit to move the lower eyelid downward to separate the upper eyelid and the lower eyelid, and a gap between two sensing units of the plurality of sensing units of the measurement apparatus is corresponding to an eye axis of the eye.

* * * * *